(12) United States Patent
Marat et al.

(10) Patent No.: US 9,464,080 B2
(45) Date of Patent: Oct. 11, 2016

(54) SUBSTITUTED PYRIDO[2,3-D]PYRIMIDINES FOR DRY SKIN AND ANTI-AGEING APPLICATION

(71) Applicant: L'OREAL, Paris (FR)

(72) Inventors: Xavier Marat, Paris (FR); Benoit Muller, Paris (FR); Agnès Thomas-Collignon, Montigny le Bretonneux (FR); Dominique Bernard, Vanves (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 14/406,365

(22) PCT Filed: Jun. 5, 2013

(86) PCT No.: PCT/IB2013/054635
§ 371 (c)(1),
(2) Date: Dec. 8, 2014

(87) PCT Pub. No.: WO2013/183017
PCT Pub. Date: Dec. 12, 2013

(65) Prior Publication Data
US 2015/0148356 A1    May 28, 2015

(30) Foreign Application Priority Data
Jun. 6, 2012 (FR) .................. 12 55267

(51) Int. Cl.
| | | |
|---|---|---|
| A61K 31/519 | (2006.01) | |
| C07D 239/70 | (2006.01) | |
| C07D 471/04 | (2006.01) | |
| A61K 8/49 | (2006.01) | |
| A61Q 19/00 | (2006.01) | |
| A61Q 19/08 | (2006.01) | |

(52) U.S. Cl.
CPC ........... *C07D 471/04* (2013.01); *A61K 8/4953* (2013.01); *A61Q 19/007* (2013.01); *A61Q 19/08* (2013.01)

(58) Field of Classification Search
CPC .......................... A61K 31/519; C07D 239/70
USPC ........................ 514/264.1; 544/279
See application file for complete search history.

(56) References Cited

U.S. PATENT DOCUMENTS

2014/0052071 A1    2/2014 Pickhard et al.

FOREIGN PATENT DOCUMENTS

| EP | 1 230 919 A2 | 8/2002 |
|---|---|---|
| FR | 10 601 83 A | 3/1954 |
| JP | S59-225188 A | 12/1984 |
| WO | 2013/183017 A1 | 12/2013 |

OTHER PUBLICATIONS

Oct. 30, 2013 International Search Report issued in Application No. PCT/IB2013/054635.
Oct. 30, 2013 Written Opinion issued in Application No. PCT/IB2013/054635.
Sarma et al. "Unexpected Deviation From Diene Behaviour of Uracil Amidine: Towards Synthesis of Some Pyrido[2,3-D]Pyrimidine Derivatives". Mol Divers, pp. 697-705, Nov. 26, 2010.
Agarwal et al. "First Report on the Abnormal Dearylation/Alkylation Reaction in One-Pot Hantzch Synthesis With 6-Amino-1,3-Dimethyl Uracil." Synthetic Communications: An International Journal for Rapid Communication of Synthetic Organic Chemistry, vol. 34, pp. 4447-4461, Aug. 6, 2004.
Pastor et al. "Synthesis and Structure of New Pyrido[2,3-D]Pyrimidine Derivatives With Calcium Channel Antagonist Activity." Tetrahedron, vol. 50, pp. 8085-8098, 1994.
Verma et al. "Thiourea Dioxide in Water as a Recyclable Catalyst for the Synthesis of Structurally Diverse Dihydropyrido[2,3-D]Pyrimidine-2,4-Diones." Tetrahedron Letters, vol. 53, pp. 2595-2600, Mar. 16, 2012.
Agarwal et al. "Dihydropyrido[2,3-D]Pyrimidines as a New Class of Antileishmanial Agents." Bioorganic & Medicinal Chemistry, vol. 13, pp. 6678-6684, Aug. 26, 2005.
Agarwal et al. "Solid Supported Synthesis of Structurally Diverse Dihydropyrido[2,3-D]Pyrimidines Using Microwave Irradiation." Tetrahedron Letters, vol. 46, pp. 1345-1358, Jan. 11, 2005.
Kajino et al. "The Hantzsch Synthesis With 6-Aminouracils: One Step Synthesis of Pyrido [2,3-D] Pyrimidines." Heterocycles, vol. 31, No. 12, pp. 2153-2161, 1990.
Matsui et al. "Saspase Regulates Stratum Corneum Hydration Through Profilaggrin-to-Filaggrin Processing." EMBO Molecular Medicine, vol. 3, pp. 320-333, 2011.

*Primary Examiner* — Douglas M Willis
(74) *Attorney, Agent, or Firm* — Oliff PLC

(57) ABSTRACT

The present invention relates to the cosmetic use, as agent for preventing and/or treating an aesthetic defect in the skin and/or its appendages that is associated with an imbalance in the differentiation and/or proliferation of the cells of an epidermis, of an effective amount of at least one compound represented by one of the general formulae, (Ia) or (Ib)

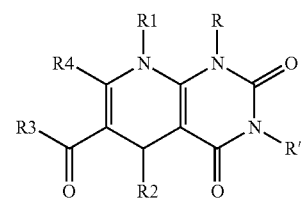

Ia

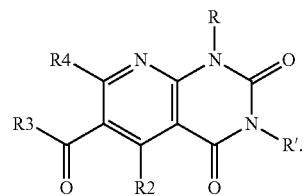

Ib

18 Claims, 3 Drawing Sheets

DMSO                    Compound (4)

DMSO    Compound (4)

SUBSTITUTED PYRIDO[2,3-D]PYRIMIDINES FOR DRY SKIN AND ANTI-AGEING APPLICATION

BACKGROUND

Figure 1:
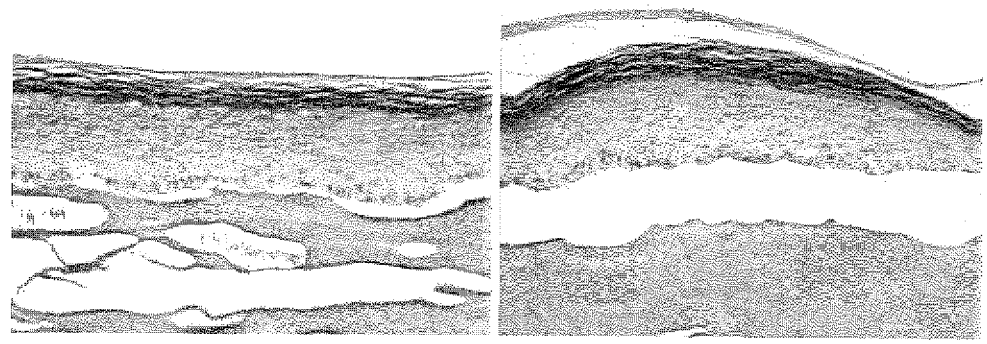

The present invention is directed to providing new compounds for preventing and/or treating a skin disorder, more particularly an aesthetic disorder of the skin. The present invention concerns more particularly the defects or disorders of the skin and/or its appendages that are linked to an imbalance in the differentiation and/or proliferation of the cells of the epidermis.

By "skin", is meant the entirety of the skin on the body, including the scalp and the mucosae. By "appendages of the skin" are meant the body hairs, eyelashes, head hair and nails.

The epidermis, the surface part of the skin, is a tissue in which the cells are joined together and interlinked with one another, and lie on a basal membrane. The epidermis forms an outer coating which comprises sebaceous or sweat glands and hair follicles. It is divided conventionally into a basal layer of keratinocytes comprising, in particular, skin stem cells, and constituting the germinal layer of the epidermis; a spinous layer consisting of a number of layers of polyhedral cells disposed on the basal layer; a "granular" layer comprising one to three layers of "flattened cells" containing distinct cytoplasmic inclusions, keratohyalin granules; and, lastly, an assembly of upper layers, referred to as the horny layer or stratum corneum (SC), consisting of keratinocytes at the terminal stage of their differentiation, referred to as corneocytes.

The stratum corneum, the outermost part of the skin, which provides the barrier function between the organism and the environment, and the hair stem, which is the emergent part of the hair follicle that constitutes the head of hair, both represent the outcome of the keratinocyte differentiation process. Epidermal differentiation follows a process of maturation in which keratinocytes in the basal layer differentiate and migrate so as to result in the formation of the corneocytes, which are dead cells that are completely keratinized. This differentiation is the result of very well coordinated phenomena which will lead to maintenance of epidermal homeostasis and will give the skin a healthy, youthful, luminous and smooth appearance.

During ageing, many physiological deteriorations in the skin occur, resulting from dysfunction of epidermal homeostasis, and in particular from dysfunction of epithelial differentiation of keratinocytes and/or of proteoglycan synthesis. The deteriorations in epidermal homeostasis are manifested primarily in a decrease in the differentiation of the keratinocytes, giving rise to a deficit in the protein matrix of the horny cells, in an increase in metalloproteases, and in their extracellular matrix-degrading activity, and also in a decrease in the synthesis of the various glycosaminoglycans. These deteriorations are also manifested, generally, in the appearance of a more marked microrelief of the skin, and even of fine lines, and eventually in the presence of deep wrinkles, a loss of elasticity, a coarse feel, and skin dryness. Histologically, a flattening of the dermal-epidermal junction and a decrease in the thickness of the dermis and epidermis are observed. The skin's collagen content and glycosaminoglycan content are also decreased, and the barrier function of the aged skin may be impaired.

Furthermore, the stratum corneum, by virtue of its solid nature and its compact, stratified structure, provides a barrier function: in particular it opposes transcutaneous water loss, also referred to as "insensible water loss". Accordingly, one of the functions of the stratum corneum is to take up and retain the water present in the epidermis, and any deterioration in SC structure and/or SC function may be manifested in changes to cutaneous moisturization. Moisturization is provided to the skin by the water in the deep-lying layers and by perspiration. A skin moisturization imbalance may be manifested in profound consequences, both physiological and cosmetic.

Cutaneous moisturization disorders, and especially skin dryness, are often observed with age and/or changes in climate. However, such conditions may also be manifested in young individuals.

The condition of skin dryness may have an acquired or non-pathological, constitutional origin, or may have a pathological constitutional origin.

Numerous external factors may lead to the skin drying out or may aggravate this condition. These factors include climate conditions such as cold or wind, solar radiation, and exposure to certain chemical or therapeutic agents.

Physiologically, dry skin is often associated with a drop in the level of skin moisturization and with an alteration in the process of maturation of the stratum corneum, the most visible sign of this being the appearance of squamae at the skin surface. In sensory terms, dry skin may be characterized by a sensation of tautness and/or of skin tension.

Many epidermal factors whose expression, biological activity or maturation are impaired, reduced or increased are known to be involved, directly or indirectly, in the incidence and manifestation of defects or disorders of the skin and/or its appendages that are linked to an imbalance in the differentiation and/or proliferation of cells of the epidermis, and more particularly of aged skin or cutaneous signs of ageing, or of dry skin or signs of skin dryness.

Furthermore, in the patent applications filed under numbers FR 10 601 83 and FR 10 601 79, a description was given of how the interaction between SASPase and FLG2 gives rise to an increase in the proteolytic activity of SASPase. This proteolytic activity is implicated in the breakdown of corneodesmosin, and, consequently, plays a part in the regulation of epidermal homeostasis, in particular through regulating phenomena of desquamation, of proliferation or of differentiation of the cells. Moreover, this function of SASPase was confirmed by the observation of its capacity to hydrolyse certain forms of filaggrin, a protein essential to the organization, function and moisturizing of the epidermal barrier (Matsui et al., EMBO Mol Med, 2011, 3:320).

The possession of active compounds, in particular pyrido-pyrimidine derivatives, capable of modulating this interaction therefore proves to be a major component in producing a cosmetic or therapeutic arsenal to counter defects or disorders of the skin and/or its appendages that are linked to an imbalance in the differentiation and/or proliferation of the cells of the epidermis.

A number of pyrido-pyrimidine derivatives are known, for example, from JP 59-225, 188, Sarma et al. (2010; Molecular Diversity; vol. 15, no. 3, pp. 697-705), Pastor (1994; Tetrahedron; vol. 50, no. 27, pp. 8085-8098), Verma et al. (2012; Tetrahedron; pp. 2595-2600); Agarwal et al. (2005; Tetrahedron Letters; vol. 46, no. 8, pp. 1345-1348), or Kajino & Meguro (1990; Heterocycles. International Journal for Reviews and Communications in Heterocyclic Chemistry; vol. 31, no. 12, pp. 2153-2161).

None of those documents teaches pyrido-pyrimidine derivatives in accordance with the invention and/or the implementation of pyrido-pyrimidine derivatives for preventing and/or treating an aesthetic defect in the skin and/or its appendages that is associated with an imbalance in the differentiation and/or proliferation of the cells of an epidermis.

It is therefore very important to find new targets, new active compounds which act on the origin of the defects or disorders in the skin and/or its appendages that are linked to an imbalance in the differentiation and/or proliferation of the cells of the epidermis.

Accordingly, there remains a need for new actives that are capable of exerting a beneficial cosmetic or therapeutic action on aged skin.

There is also a need for new actives that are capable of exerting a preventive and/or care action with regard to aged skin, this action being durable over time.

There further exists a need for new actives or new treatments for promoting and/or reinforcing the moisturizing of the skin.

There is also a need for new actives or new treatments for preventing and/or treating dry skin or signs of skin ageing.

SUMMARY

The object of the present invention is to meet these needs.

Accordingly, in accordance with a first object, the invention relates to the cosmetic use, as agent for preventing and/or treating an aesthetic defect in the skin and/or its appendages that is associated with an imbalance in the differentiation and/or proliferation of the cells of an epidermis, of an effective amount of at least one compound represented by one of the general formulae, (Ia) or (Ib):

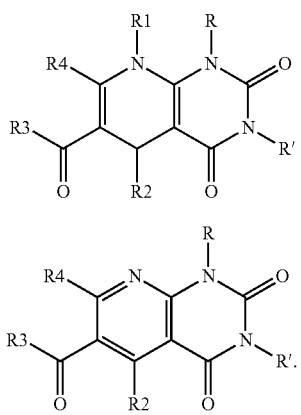

in which:
$R^1$ represents H; —C(O)$R^{10}$, with $R^{10}$ representing a saturated or unsaturated, linear or branched $C_1$-$C_4$, or even $C_2$-$C_3$, alkyl, or a phenyl;
$R^2$ represents H; a saturated or unsaturated, linear or branched $C_1$-$C_{12}$, more particularly $C_1$-$C_6$, or even $C_2$-$C_4$ alkyl group; or a group selected from:

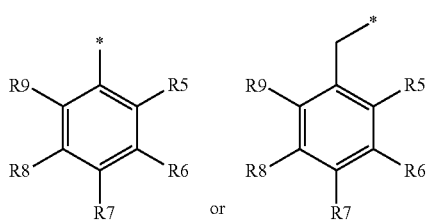

in which $R^5$, $R^6$, $R^7$, $R^8$ and $R^9$ represent, independently of one another, H; —$NO_2$; —OH; O$R^{10}$; —CN; a fluorine; Cl; I; Br; —$CF_3$; a saturated or unsaturated, linear or branched $C_1$-$C_4$ alkyl; a phenyl; —OC(O)—$R^{10}$; —O-Ph-X with X representing H, —OH, —$NO_2$, a fluorine, a saturated or unsaturated, linear or branched $C_1$-$C_4$, or even $C_2$-$C_3$, alkoxy or alkyl; with $R^{10}$ being as defined above,
$R^3$ represents a group —O$R^{11}$, with $R^{11}$ being H, a saturated or unsaturated, linear or branched $C_1$-$C_4$, or even $C_2$-$C_3$, alkyl, or a phenyl,
$R^4$ represents a saturated or unsaturated, linear or branched $C_1$-$C_4$, $C_2$-$C_4$, or even $C_2$-$C_3$, alkyl; or a phenyl,
R and R', which are identical or different, represent H or a linear or branched $C_1$-$C_4$, or even $C_2$-$C_3$, alkyl,
or a physiologically acceptable salt of said compound.

The inventors have observed, unexpectedly, that compounds of these kinds, in particular, are endowed with strong proproliferative properties and, in particular, induce an increase in CD44. Taken together, therefore, these properties make the compounds of the invention particularly effective against defects or disorders of the skin and/or its appendages that are linked to an imbalance in the differentiation and/or proliferation of the cells of an epidermis.

Using a compound of the invention allows a youthful appearance to be restored to and/or conferred on a person's skin.

According to another advantage, use in accordance with the invention may reduce and/or treat the signs of skin ageing.

According to another advantage, use in accordance with the invention may promote maintenance of the homeostasis and/or barrier properties of an aged skin.

According to another of its aspects, the present invention relates to a compound of the invention, in effective amount in a pharmaceutical or dermatological composition, for preventing and/or treating pathological constitutional dry skin selected from atopic dermatitis and ichthyosis.

According to another of its aspects, the present invention relates to a cosmetic method for preventing and/or treating an aesthetic defect in the skin and/or its appendages that is linked to an imbalance in the differentiation and/or proliferation of the cells of an epidermis in an individual in need thereof, comprising at least one step of administering to said individual at least an effective amount of at least one compound of the invention.

According to another of its aspects, the present invention relates to a compound represented by the general formula (IIa):

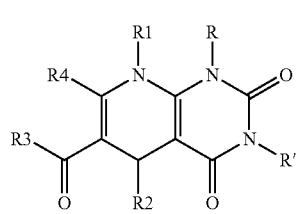

in which:
$R^1$ represents H, and
$R^2$ represents a saturated, linear or branched $C_1$-$C_4$, or even $C_2$-$C_3$, alkyl; or

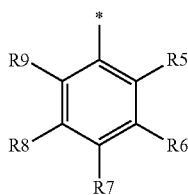

in which $R^5$, $R^6$, $R^7$, $R^8$ and $R^9$ represent, independently of one another, H; —OH; $OR^{10}$, with $R^{10}$ representing a saturated or unsaturated, linear or branched $C_1$-$C_4$, or even $C_2$-$C_3$, alkyl, or a phenyl, $R^3$ represents a group —$OR^{11}$, with $R^{11}$ representing H, or a saturated or unsaturated, linear or branched $C_1$-$C_2$ alkyl;

$R^4$ represents a saturated, linear or branched $C_1$-$C_4$, $C_2$-$C_4$, or even $C_2$-$C_3$, alkyl, R and R', which are identical or different, represent H or a methyl, or a physiologically acceptable salt of said compound.

According to another of its aspects the invention relates to a compound, as such, represented by the general formula (IIa):

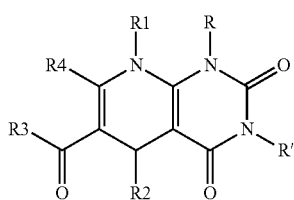

in which:
$R^1$ represents H, and
$R^2$ represents a saturated, linear or branched $C_1$-$C_4$, or even $C_2$-$C_3$, alkyl; or

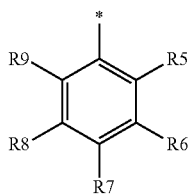

in which $R^5$, $R^6$, $R^7$, $R^8$ and $R^9$ represent, independently of one another, H; —OH; $OR^{10}$, with $R^{10}$ representing a saturated or unsaturated, linear or branched $C_1$-$C_4$, or even $C_2$-$C_3$, alkyl, or a phenyl, $R^3$ represents a group —$OR^{11}$, with $R^{11}$ representing H, or a saturated or unsaturated, linear or branched $C_1$-$C_2$ alkyl;

$R^4$ represents a saturated, linear or branched $C_2$-$C_4$, or even $C_2$-$C_3$ alkyl, R and R', which are identical or different, represent H or a methyl, or a physiologically acceptable salt of said compound.

According to another of its aspects, the present invention relates to a cosmetic or dermatological composition comprising, in a physiologically acceptable medium, an effective amount of at least one compound of general formula (IIa) as defined above, and more particularly hereinafter.

DETAILED DESCRIPTION OF EMBODIMENTS

In the sense of the present invention, the term "prevent" means reducing a risk of appearance or reducing a probability of incidence of the phenomenon in question.

In the sense of the present invention, "effective amount" of a compound of the invention means an amount of this compound that is sufficient and necessary for exerting a preventing and/or treatment effect on defects or disorders of the skin and/or its appendages that are linked to an imbalance in the differentiation and/or proliferation of the cells of an epidermis. Such an amount may be determined by any method known to the skilled person, as for example by means of tests in vitro, ex vivo or in vivo, such as clinical trials.

In the sense of the present invention, a "physiologically or cosmeceutically or pharmaceutically acceptable medium" means a medium compatible with administration to a person, more particularly to the skin and its appendages of said person.

Within the present invention, an alkyl or alkoxy of a certain length encompasses all individual sub-ranges of alkyl or alkoxy. Accordingly, and in a non-limitative way, a $C_1$-$C_{12}$ alkyl or alkoxy encompasses a $C_1$-$C_{12}$; a $C_1$-$C_{11}$; a $C_1$-$C_{10}$; a $C_1$-$C_9$; a $C_1$-$C_8$; a $C_1$-$C_7$; a $C_1$-$C_6$; a $C_1$-$C_5$; a $C_1$-$C_4$; a $C_1$-$C_3$; a $C_1$-$C_2$; a $C_2$-$C_4$; or a $C_2$-$C_3$ alkyl or alkoxy.

Accordingly, a $C_1$-$C_4$ alkyl or alkoxy encompasses a $C_1$-$C_4$; a $C_1$-$C_3$; a $C_1$-$C_2$; a $C_2$-$C_4$; a $C_2$-$C_3$ or a $C_3$-$C_4$ alkyl or alkoxy.

Defects or Disorders of the Skin and/or its Appendages that are Linked to an Imbalance in the Differentiation and/or Proliferation of the Cells of an Epidermis The compounds of the invention are found particularly advantageous in preventing and/or treating defects or disorders of the skin and/or its appendages that are linked to an imbalance in the differentiation and/or proliferation of the cells of an epidermis.

Depending on the degree of intensity of the appearance of these disorders or defects, they may arise from aesthetic disorders or defects of the skin or from pathological disorders or defects of the skin. Such classification is part of the skills of a skilled person.

The disorders or defects of the skin more particularly in question in the present invention are those associated with aged and/or dry skins.

According to one embodiment, the compounds of the invention are especially suitable for preventing and/or treating aged skin and/or cutaneous signs of ageing, a disorder of the barrier function of the epidermis, or a dry skin and/or signs of skin dryness.

Aged Skin

By "aged skin" is meant a general condition of the skin that results from chronological ageing and/or from photo-induced ageing.

By "cutaneous signs of ageing" are meant all modifications of the external appearance of the skin that are caused by ageing, whether chronological and/or photo-induced in its origin.

Depending on the degree of intensity of the appearance of a skin disorder associated with aged skin, the disorder may lie in an aesthetic disorder of the skin or a pathological disorder of the skin. Such classification is within the skills of the skilled person.

Examples of these modifications contemplated in the invention include any modifications of the external appearance of the skin that are caused by ageing, whether chronological and/or photo-induced ageing, as for example wrinkles and fine lines, withered skin, slack skin, lack of elasticity and/or tone in the skin, emaciation of the dermis and/or breakdown of the collagen fibres, giving the skin a flabby and wrinkled appearance.

According to one preferred embodiment, the compounds of the invention are especially suitable for preventing, reducing and/or treating wrinkles, fine lines or a deterioration in the microrelief.

Also contemplated in the present invention are all internal modifications of the skin that are not systematically manifested in a modified external appearance, as for example all internal degradations of the skin, and more particularly the breakdown of elastin fibres, or elastic fibres, as a result of exposure to ultraviolet radiation.

According to another preferred embodiment, the compounds of the invention are especially suitable for reinforcing the mechanical properties of the skin, more particularly for combating withered, flabby, slackened, sunken and/or emaciated skin, and/or for reinforcing and/or restoring the elasticity or firmness of the skin.

According to another preferred embodiment, the cutaneous signs of ageing to which the invention is directed may be selected from emaciation of the skin, a loss of firmness, a loss of elasticity, a loss of density, or a loss of tonicity in the skin, the appearance of a marked microrelief of the skin, the formation and/or presence of fine lines and/or wrinkles, a deterioration in the complexion of the skin, a wizened appearance of the skin, a deterioration in the odour of the skin, a sinking of the skin, or a withering of the skin.

The skin signs of ageing to which the invention is directed are preferably selected from emaciation of the skin, the appearance of a marked microrelief of the skin, the formation and/or presence of fine lines and/or wrinkles, sinking of the skin, and withering of the skin.

More preferably still, the skin signs of ageing to which the invention is directed are selected from the appearance of a marked microrelief of the skin, the formation and/or presence of fine lines and/or wrinkles, sinking of the skin, and withering of the skin.

More particularly, the skin signs of ageing to which the invention is directed concern emaciation of an epidermis and/or a loss of firmness, elasticity, density and/or tonicity of an epidermis and/or the formation of wrinkles and fine lines.

Dry Skin

By "skin moisturization" is meant the entirety of the cellular and molecular mechanisms which result in providing and maintaining the presence of an amount of physiological water in the epidermis and the dermis, and also the resulting amount of water.

According to one aspect, the invention aims to maintain or even stimulate the homeostasis of these mechanisms, and thereby to promote and/or reinforce skin moisturization. Accordingly, in accordance with one aspect, the invention applies to skin which has a physiological moisturized state, also classed as normal.

According to another aspect, the invention aims to restore the balance and/or reduce the risk of incidence of an imbalance in the homeostasis of these mechanisms, and thereby to prevent and/or treat dry skin and/or the signs of skin dryness.

By "dry skin" is meant a general state of the skin that results from a deficit of water in the epidermis and/or dermis.

By "signs of skin dryness" are meant all of the modifications to the appearance of the skin that are caused by a deficit of water in the epidermis and/or dermis.

Depending on the degree of manifestation of the deficit in water of the skin, a dry skin may appear coarse to the touch, wrinkled, or even covered with squamae. A dry skin may be manifested, essentially, in a sensation of tautness and/or tension.

Dry skin may be manifested in a desquamation disorder and may present different stages depending on the severity of this desquamation.

When the skin is slightly dry, these squamae are abundant but barely visible to the naked eye, with removal taking place corneocyte by corneocyte. These squamae are increasingly few in number, but increasingly visible to the naked eye, as this disorder worsens; the masses may comprise several hundred corneocytes, thus representing more or less large masses, called squamae.

Dryness of the skin may be constitutional or acquired.

In the case of constitutional dry skin, there are two categories that may be distinguished: pathological skin and non-pathological skin.

Pathological constitutional dry skin is essentially represented by atopic dermatitis and ichthyosis. It is virtually independent of the external conditions and its origin is known or unknown genetic modifications. The known genetic modifications that affect skin moisturization include, for example, modifications of the transglutaminase-1 gene or modifications of the filaggrin gene.

According to one embodiment, the compounds of the invention are especially suitable for preventing and/or treating pathological constitutional dry skin selected from atopic dermatitis and ichthyosis.

In the case of non-pathological constitutional dry skin, the severity of the state of dryness may itself be dependent on external factors. Included in this skin category are senile skin (characterized by a general decrease in cutaneous metabolism with age), fragile skin (highly sensitive to external factors and often accompanied by erythema and rosacea) and common xerosis (of probable genetic origin, and manifested primarily on the face, the limbs and the back of the hands).

In the case of acquired dry skin, the intervention of external parameters such as exposure to chemical agents, to adverse climatic conditions, to solar radiation or else to certain therapeutic treatments (retinoids, for example) is a determining factor. Under these external influences, the epidermis may then become temporarily and locally dry. This may affect any type of epidermis.

Irrespective of the origin, skin afflicted by dryness may present, generally speaking, the following signs: an appearance which is coarse to the touch and scaly, and reduced suppleness and elasticity.

Dry skin, also called "xerosis", may appear at any age, and may not be linked to a pathological condition. In this case, it is referred to as "acquired" dryness.

Xerosis, however, becomes more frequent and troublesome with age, especially in women. It is then referred to as senile xerosis. Furthermore, women generally suffer an aggravation of the skin dryness during menopause, probably owing to the hormonal disordering that is a characteristic of this phenomenon. Those areas most heavily affected are the lower part of the legs, the dorsal part of the forearms, and the hands.

As mentioned above, acquired dryness may be subject to external factors. For example, the appearance of dry skin may be promoted by cold, dry and wintry weather. It is then referred to as winter xerosis. Skin dryness may also be induced by exogenous stress, of chemical origin, such as of anionic detergent type, for example, or else of mechanical origin (rubbing, shaving).

According to one embodiment, the cosmetic use of the invention may advantageously be suitable for preventing and/or treating senile or fragile dry skin, or xerosis, selected in particular from common xerosis, senile xerosis and winter xerosis.

According to one embodiment, dry skin contemplated in the invention may be more particularly young skin.

Although no study has demonstrated any effect of dryness on the origin and formation of the wrinkles and fine lines which are essentially attributable to ageing, from a visual standpoint, dry skin makes such features more apparent. Dry skin may therefore be young or aged skin with wrinkles or fine lines. The wrinkles and fine lines subsequent to skin dryness are therefore not associated with skin ageing.

Furthermore, from a sensory standpoint, skin dryness is characterized by a sensation of tautness and/or itching. For obvious reasons, these manifestations are not only a source of discomfort, or even pain, but also have an unattractive appearance.

According to one embodiment, the cosmetic use of the invention may advantageously be suitable for preventing and/or treating dry skin-associated itching and/or pulling sensations.

Examples of signs of skin dryness that are contemplated in the invention include withered skin, lack of elasticity, suppleness and/or tone in the skin, coarse feel, the presence of cracks, desquamation, the presence of scales, or dry skin-associated wrinkles and fine lines.

Compounds

According to one embodiment, a compound more particularly contemplated according to the invention may be represented by one of the general formulae (Ia) or (Ib), as defined above.

According to one preferred embodiment, a compound of the invention may be represented by the general formula (Ia) in which:
$R^1$ represents H,
$R^2$ represents H; a saturated or unsaturated, linear or branched $C_1$-$C_{12}$, more particularly $C_1$-$C_6$, or even $C_2$-$C_4$ alkyl group; or a group selected from:

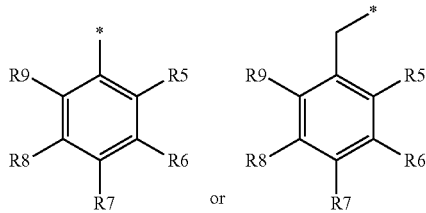

in which $R^5$, $R^6$, $R^7$, $R^8$ and $R^9$ represent, independently of one another, H; —$NO_2$; —OH; $OR^{10}$; —CN; a fluorine; Cl; I; Br; —$CF_3$; a saturated or unsaturated, linear or branched $C_1$-$C_4$, or even $C_2$-$C_3$, alkyl; a phenyl; —OC(O)—$R^{10}$; —O-Ph-X with X representing H, —OH, —$NO_2$, a fluorine, a saturated or unsaturated, linear or branched $C_1$-$C_4$, or even $C_2$-$C_3$, alkoxy or alkyl;
$R^3$ represents a group $OR^{11}$,
$R^4$ represents a saturated or unsaturated, linear or branched $C_1$-$C_4$, $C_2$-$C_4$, or even $C_2$-$C_3$, alkyl; or a phenyl, $R^{10}$ represents a saturated or unsaturated, linear or branched $C_1$-$C_4$ alkyl; or a phenyl, and $R^{11}$ represents H; or a saturated or unsaturated, linear or branched $C_1$-$C_4$ alkyl; or a phenyl,
R and R', which are identical or different, represent H or a methyl,
or a physiologically acceptable salt of said compound.

According to yet another preferred embodiment, a compound of the invention may be represented by the general formula (Ia) in which:
$R^1$ represents H,
$R^2$ represents H; a saturated or unsaturated, linear or branched $C_1$-$C_{12}$, more particularly $C_1$-$C_6$, or even $C_2$-$C_4$ alkyl group; or a group selected from:

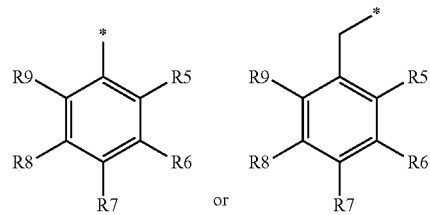

in which $R^5$, $R^6$, $R^7$, $R^8$ and $R^9$ represent, independently of one another, H; —OH; $OR^{10}$; —CN; a saturated or unsaturated, linear or branched $C_1$-$C_4$ alkyl; or a phenyl;
$R^3$ represents a group-$OR^{11}$,
$R^4$ represents a saturated, linear or branched $C_1$-$C_4$, $C_2$-$C_4$, or even $C_2$-$C_3$, alkyl,
$R^{10}$ represents a saturated or unsaturated, linear or branched $C_1$-$C_4$ alkyl; or a phenyl, and $R^{11}$ represents H; or a saturated or unsaturated, linear or branched $C_1$-$C_4$ alkyl; or a phenyl,
R and R', which are identical or different, represent H or a methyl,
or a physiologically acceptable salt of said compound.

According to yet another preferred embodiment, a compound of the invention may be represented by the general formula (Ia) in which:
$R^1$ represents H,
$R^2$ represents a saturated or unsaturated, linear or branched $C_1$-$C_6$, or even $C_2$-$C_4$, alkyl group; or a group selected from

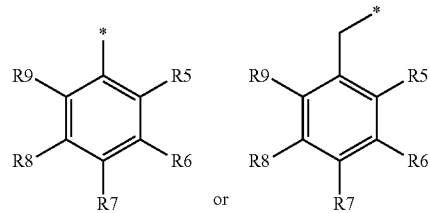

in which $R^5$, $R^6$, $R^7$, $R^8$ and $R^9$ represent, independently of one another, H; —OH; —$OR^{10}$; —CN; a saturated or unsaturated, linear or branched $C_1$-$C_3$ alkyl, with $R^{10}$ being a saturated or unsaturated, linear or branched $C_1$-$C_3$ alkyl, or being a phenyl,
$R^3$ represents a group —$OR^{11}$, with $R^{11}$ being H, a saturated or unsaturated, linear or branched $C_1$-$C_4$, or even $C_2$-$C_3$, alkyl, R and R', which are identical or different, represent H or a saturated or unsaturated, linear or branched $C_1$-$C_3$ alkyl, or a physiologically acceptable salt of said compound.

According to yet another preferred embodiment, a compound of the invention may be represented by the general formula (Ia) in which:

$R^1$ represents H, $R^2$ represents a saturated, linear or branched $C_1$-$C_6$, or even $C_2$-$C_4$, alkyl group, and preferably represents a methyl, an ethyl, an n-propyl, an isopropyl, an n-butyl, a sec-butyl, an isobutyl, a tert-butyl, and preferably an isobutyl; a group

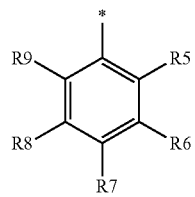

in which $R^5$, $R^6$, $R^7$, $R^8$ and $R^9$ represent, independently of one another, H; —OH; —$OR^{10}$; —CN, with $R^{10}$ being a saturated or unsaturated, linear or branched $C_1$-$C_2$ alkyl, and preferably a methyl, or being a phenyl; or a group

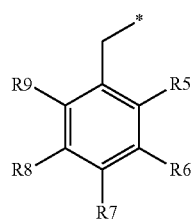

in which $R^5$, $R^6$, $R^7$, $R^8$ and $R^9$ represent H $R^3$ represents a group —$OR^{11}$, with $R^{11}$ being H, a saturated, linear or branched $C_1$-$C_4$, or even $C_2$-$C_3$, alkyl, R and R', which are identical or different, represent H or a saturated or unsaturated, linear or branched $C_1$-$C_2$ alkyl, and preferably a methyl, or a physiologically acceptable salt of said compound.

According to yet another preferred embodiment, a compound of the invention may be represented by the general formula (Ia) in which:

$R^1$ represents H, $R^2$ represents a saturated, linear or branched $C_1$-$C_6$, or even $C_2$-$C_4$, alkyl group, and preferably represents a methyl, an ethyl, an n-propyl, an isopropyl, an n-butyl, a sec-butyl, an isobutyl, a tert-butyl, and preferably an isobutyl; a group

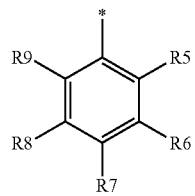

in which $R^5$, $R^6$, $R^7$, $R^8$ and $R^9$ represent, independently of one another, H; —OH; —$OR^{10}$; —CN, with $R^{10}$ being a saturated or unsaturated, linear or branched $C_1$-$C_2$ alkyl, and preferably a methyl, or being a phenyl;

$R^3$ represents a group —$OR^{11}$, with $R^{11}$ being H, a saturated, linear or branched $C_1$-$C_4$, or even $C_2$-$C_3$, alkyl, R and R', which are identical or different, represent H or a saturated or unsaturated, linear or branched $C_1$-$C_2$ alkyl, and preferably a methyl, or a physiologically acceptable salt of said compound.

More preferably $R^2$ may represent a group selected from:

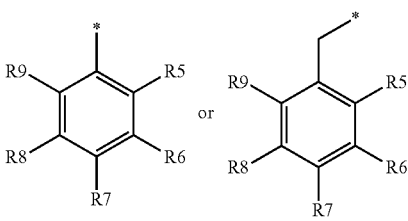

in which $R^5$ and $R^9$ represent H and $R^6$, $R^7$ and $R^8$ represent, independently of one another, a group as defined above, and preferably H; —OH; —$OR^{10}$; —CN, with $R^{10}$ being a saturated or unsaturated, linear or branched $C_1$-$C_2$ alkyl, and preferably a methyl, or being a phenyl.

According to yet another preferred embodiment, a compound of the invention may be represented by the general formula (Ia) in which:

$R^1$ represents H, $R^2$ represents H, a saturated or unsaturated, linear or branched $C_1$-$C_6$, or even $C_2$-$C_4$, alkyl group, $R^3$ represents a group —$OR^{11}$, with $R^{11}$ being H, or a linear or branched $C_1$-$C_4$, or even $C_2$-$C_3$, alkyl, $R^4$ represents a methyl, R and R' represent a methyl, or a physiologically acceptable salt of said compound.

According to yet another preferred embodiment, a compound of the invention may be selected from:

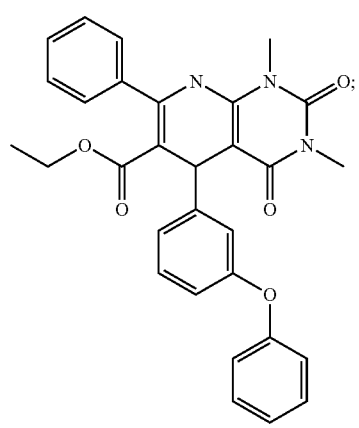

(1)

(2)
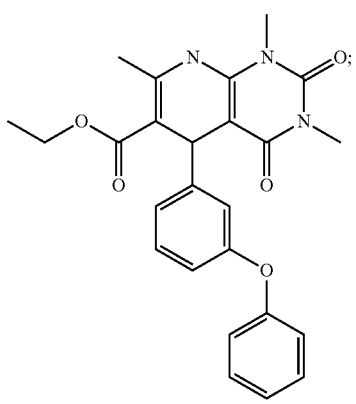

(3)
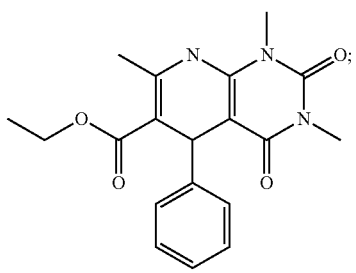

(4)
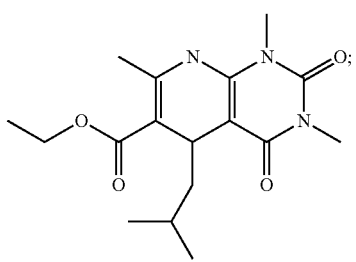

(5)
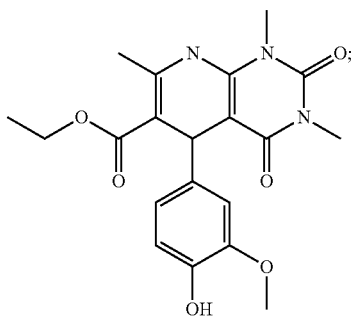

(6)
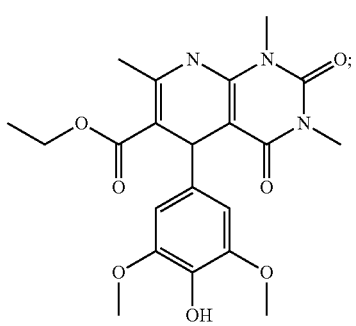

(7)
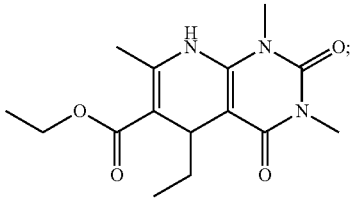

(8)
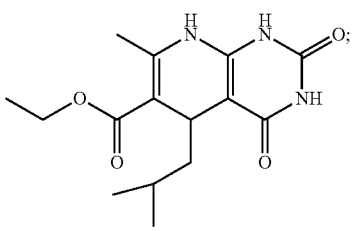

(9)
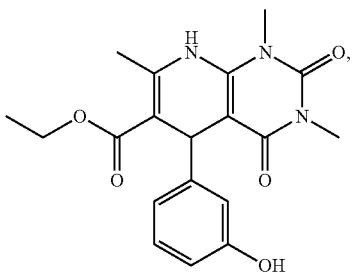

or a physiologically acceptable salt of said compound.

The invention likewise provides, as such, a compound represented by the general formula (IIa):

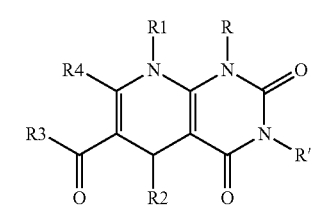

IIa in which:
$R^1$ represents H, and
$R^2$ represents a saturated, linear or branched $C_1$-$C_4$, or even $C_2$-$C_3$, alkyl; or

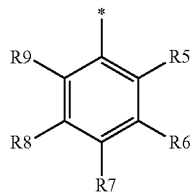

in which $R^5$, $R^6$, $R^7$, $R^8$ and $R^9$ represent, independently of one another, H; —OH; $OR^{10}$, with $R^{10}$ representing a saturated or unsaturated, linear or branched $C_1$-$C_4$, or even $C_2$-$C_3$, alkyl, or a phenyl, $R^3$ represents a group —$OR^{11}$, with $R^{11}$ representing H, or a saturated or unsaturated, linear or branched $C_1$-$C_2$ alkyl;

$R^4$ represents a saturated, linear or branched $C_1$-$C_4$, $C_2$-$C_4$, or even $C_2$-$C_3$, alkyl, R and R', which are identical or different, represent H or a methyl, or a physiologically acceptable salt of said compound.

According to another of its aspects the invention relates to a compound, as such, represented by the general formula (IIa):

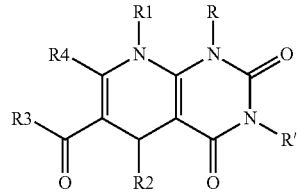

(IIa)

in which:

$R^1$ represents H, and $R^2$ represents a saturated, linear or branched $C_1$-$C_4$, or even $C_2$-$C_3$, alkyl; or

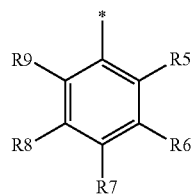

in which $R^5$, $R^6$, $R^7$, $R^8$ and $R^9$ represent, independently of one another, H; —OH; $OR^{10}$, with $R^{10}$ representing a saturated or unsaturated, linear or branched $C_1$-$C_4$, or even $C_2$-$C_3$, alkyl, or a phenyl, $R^3$ represents a group —$OR^{11}$, with $R^{11}$ representing H, or a saturated or unsaturated, linear or branched $C_1$-$C_2$ alkyl;

$R^4$ represents a saturated, linear or branched $C_2$-$C_4$, or even $C_2$-$C_3$ alkyl, R and R', which are identical or different, represent H or a methyl, or a physiologically acceptable salt of said compound.

More particularly the invention relates to a compound, as such, selected from:

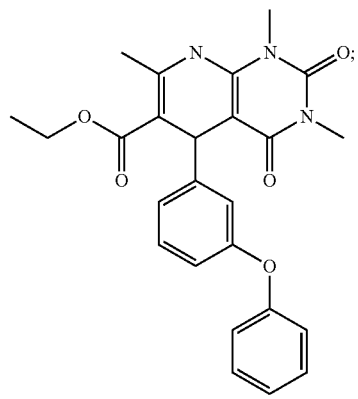

(2)

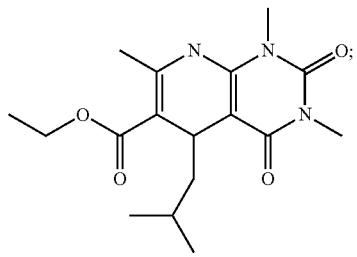

(4)

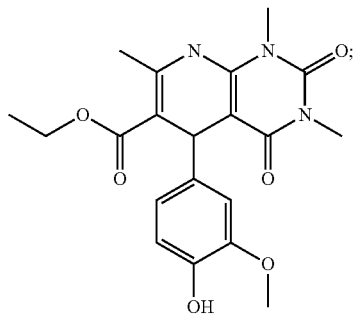

(5)

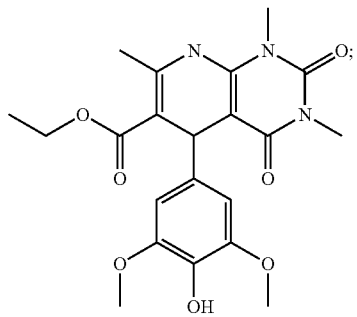

(6)

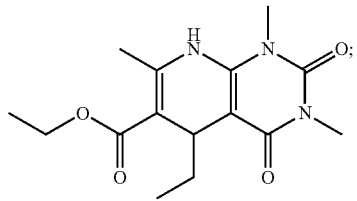

(7)

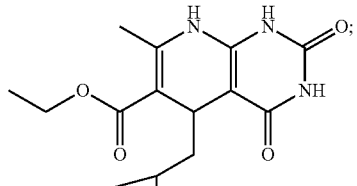

(8)

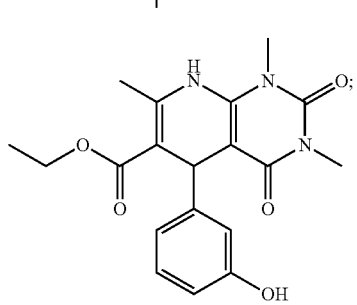

(9)

or a physiologically acceptable salt of said compound.

More preferably the invention provides, as such, a compound selected from:

(2)
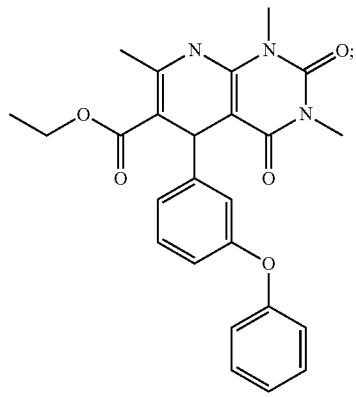

(4)
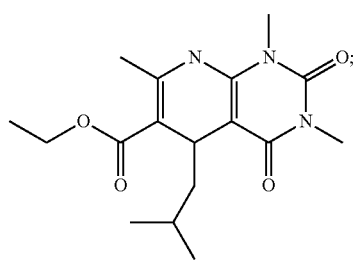

(5)
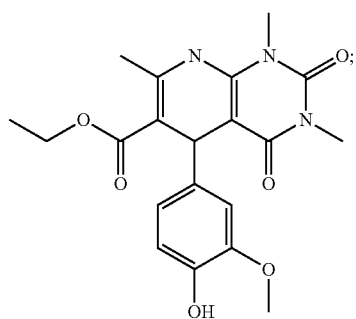

(6)
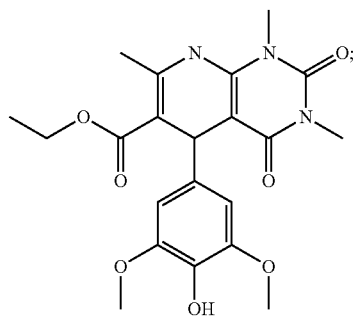

(7)
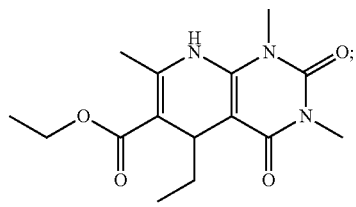

(8)
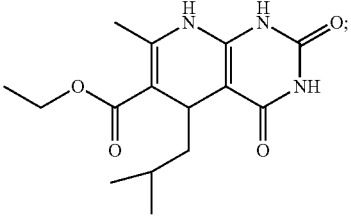

or a physiologically acceptable salt of said compound.

According to one embodiment, the compounds (1), (2), (3), and (4) are preferred according to the present invention. More preferably still, the compounds (2), (3), and (4) are more particularly contemplated in the present invention.

According to one preferred embodiment, a compound of the invention may be selected from compounds (2) and (4) to (8).

A physiologically acceptable salt of a compound of general formula (Ia), (Ib), or (IIa) according to the invention may be a salt of a compound of general formula (Ia), (Ib), or (IIa) and of an alkali metal, an alkaline earth metal, or ammonium, comprising the salts obtained with organic ammonium bases, or salts of a compound of general formula (Ia), (Ib), or (IIa) and of an organic or inorganic acid.

Salts suitable more particularly for the invention may be sodium, potassium, calcium or magnesium salts, quaternary ammonium salts such as tetramethylammonium or tetraethylammonium, and addition salts with ammonia and with physiologically acceptable organic amines, such as methylamine, dimethylamine, trimethylamine, ethylamine, triethyl-amine, ethanolamine or tris(2-hydroxyethyl)amine.

Salts of a compound of general formula (Ia), (Ib), or (IIa) and of an inorganic acid that are suitable for the invention may be obtained with hydrochloric acid, hydrobromic acid, sulfuric acid, nitric acid or phosphoric acid.

Salts of a compound of general formula (Ia), (Ib), or (IIa) and of an organic acid that are suitable for the invention may be obtained with carboxylic acids and sulfonic acids, such as formic acid, acetic acid, oxalic acid, citric acid, lactic acid, malic acid, succinic acid, malonic acid, benzoic acid, maleic acid, fumaric acid, tartaric acid, methanesulfonic acid, benzenesulfonic acid or p-toluenesulfonic acid.

A compound of the invention may be employed at from 0.01 to 10% by weight, preferably from 0.1 to 5% by weight, relative to the total weight of the composition comprising it.

Compounds of the invention may be obtained by any method known to the skilled person.

More particularly, the pyridopyrimidinetrione derivatives of the invention may be obtained by means of the Hantzsch reaction, allowing a single-step synthesis. The Hantzsch reaction is known in the literature (in particular *Bioorg. Med. Chem.* 2005, 13, 6678-6684), and is shown schematically below:

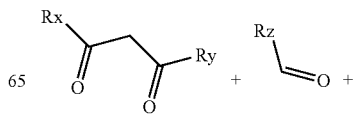

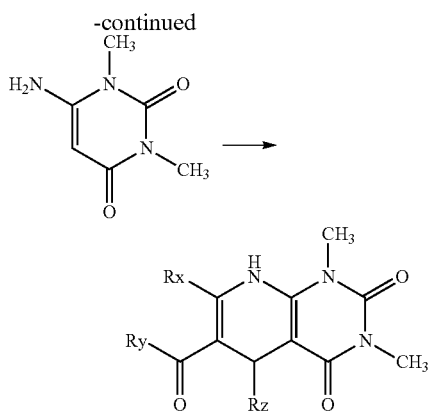

These compounds may be obtained using a Radley system, under an inert atmosphere, with cooling equipment and a hotplate fitted with magnetic stirring. Various methods of treatment and purification may be applied.

The Hantzsch reaction may sometimes result in oxidized compounds: a dearylated product and/or dehydrogenated product (pyridine skeleton). In certain cases, therefore, a supplementary reduction step, implemented for example with a reducing agent such as $NaBH_4$, may be performed.

Compositions

A compound of the invention is advantageously formulated in a composition that may be in any of the formulations normally available for the indication in question and for the administration route in question.

A composition according to the invention comprises a physiologically or pharmaceutically acceptable medium.

A composition according to the invention may be administered orally, topically, or intradermally or subcutaneously, and preferably topically.

According to one embodiment, a topical composition according to the invention may advantageously be formulated in any formulation suitable for caring for the skin and its appendages, and may take the form of ointments, creams, solutions, gels, emulsions, foams or aerosol compositions containing a propellant, milks, pomades, powders, impregnated pads, lotions or suspensions. They may also take the form of microspheres or nanospheres or of lipid or polymeric vesicles or polymeric patches and hydrogels that allow controlled release. These compositions may take an anhydrous or aqueous form depending on the dermocosmetic indication in question.

A composition intended for topic administration may be an aqueous, aqueous-alcoholic or oily solution, a solution or dispersion in the form of a lotion or serum, a milk emulsion with a liquid or semi-liquid consistency, obtained by dispersing a fatty phase in an aqueous phase (O/W) or vice versa (W/O), a suspension or emulsion with a soft, semi-solid or solid consistency, as a cream or as an aqueous or anhydrous gel, a multiple (W/O/W or O/W/O) emulsion, a microemulsion, a nanoemulsion, a preparation of microcapsules, a preparation of microparticles, or an ionic and/or nonionic vesicle dispersion, or a wax/aqueous phase dispersion.

According to one embodiment, a composition of the invention may also take the form of a transdermal system allowing active or passive release of the active or actives transdermally, such as a patch or gel patch (hydrogel), for example.

These compositions are prepared according to the usual methods.

In the case of a composition in accordance with the invention for oral administration, preference is given to the use of an ingestible vehicle of a kind suitable for the type of composition in question. Suitable in particular, accordingly, as food vehicles are coated tablets, gelatin capsules or tablets, suspensions, oral supplements in dry form and oral supplements in liquid form, milk, yogurt, cheese, fermented milks, fermented milk-based products, ice creams, cereal-based products or products based on fermented cereals, milk-based powders, infant and baby formulas, confectionery products, chocolate, cereals, or animal feeds, more particularly for domestic animals.

An oral composition means, for example, nutritional, nutraceutical, cosmeceutical or pharmaceutical compositions comprising at least one compound according to the invention.

The oral compositions according to the invention may be formulated by any usual method known to the skilled person for producing drinkable solutions, coated tablets, gelatin capsules, gels, emulsions, tablets for swallowing or crunching, capsules, especially soft or hard capsules, granules to be dissolved, syrups, solid or liquid foods, and hydrogels that allow controlled release, food bars, compact or uncompacted powders, liquid suspensions or solutions, confectionery, fermented milk, fermented cheeses, chewing gums, dentifrice pastes or spray solutions.

The oral compositions may take an anhydrous form or an aqueous form, depending on the dermocosmetic indication.

A compound of the invention, furthermore, may be formulated with the excipients and ingredients usual for such oral compositions or food supplements, namely, in particular, fatty and/or aqueous ingredients, humectants, thickeners, preservatives, texturizers, flavours and/or coating agents, and/or antioxidants.

The formulating agents and excipients for oral compositions, and especially for food supplements, are known in this field and are not the subject of a detailed description here.

According to another embodiment, a compound suitable for the invention may be employed subcutaneously or intradermally.

In the case of such use, an active suitable for the invention may be packaged in the form of a sterile aqueous or non-aqueous isotonic solution, in the form of a dispersion, suspension or emulsion which, where appropriate, is prepared immediately prior to administration, starting from a sterile—for example, lyophilized—powder, which is then made up into the form of an injectable sterile solution or a dispersion at the time of its use.

"Sterile" refers to a formulation able to guarantee the harmlessness required for intraepidermal and/or intradermal and/or subcutaneous administration.

A composition suitable for the invention may comprise any excipient commonly used in the field of injectable sterile solutions.

A composition of the invention may be administered by any technique and/or injection device suitable for intraepidermal injection and/or intradermal injection and/or subcutaneous injection. Accordingly, such administration may take place by mesotherapy.

For the intradermal route, preference may be given to administration by systemic patch.

A composition according to the invention may further comprise any formulating agent or any additional active that is cosmetically or dermatologically acceptable. The amounts of these various agents or actives are those conventionally used in the field in question, and are determined in particular so as not to be detrimental to the properties desired for a compound of the invention or for a composition of the invention.

A cosmetic or dermatological active suitable for the invention may be selected from moisturizers, pro-desquamating agents, vitamins, essential fatty acids, hydroxyacids, sulfated polysaccharides, sphingolipids, UV filters, antioxidants, anti-acne agents, anti-inflammatory agents, agents for tanning (in the absence of UV radiation), depigmenting agents, matting agents, proteins or protein hydrolysates, probiotics, amino acids, polyols, urea and derivatives thereof, jasmonic acid and derivatives thereof, allantoin, sugars and sugar derivatives, water-soluble vitamins, plant extracts and hydroxy acids, retinol and derivatives thereof, tocopherol and derivatives thereof, essential fatty acids, ceramides, essential oils, salicylic acid and derivatives thereof, vitamin D3 and derivatives thereof, retinoids and derivatives thereof, PPAR-gamma agonists, agents for preventing hair loss or stimulating hair growth, such as potassium channel openers, antidandruff agents, anti-androgens, proxylan and derivatives thereof, and mixtures of these actives.

A composition of the invention may comprise any formulating agent commonly used in the field. Examples of formulating agents suitable for the invention include hydrophilic gellants, lipophilic gellants, surfactants, fillers, odour absorbers, colorants, film-forming polymers, fatty materials such as volatile or non-volatile oils, fatty substances in the form of pastes or solids, such as waxes or gums, solvents, such as ethanol or propylene glycol, or a spring water and/or mineral water.

Packaging Article

A packaging article of the invention will naturally be selected by the skilled person in accordance with the formulation of the composition to be packaged.

Accordingly, for liquid compositions, use may be made of containers composed of a rigid casing comprising means for distributing the composition. These distributing means may be a simple orifice, closed with a removable cap, or a pushbutton in combination with a pump that allows a portion of the composition present in the container to be expelled. The compositions of the invention in liquid form may also be packaged in aerosol can containers.

A composition of the invention in semi-liquid or paste-like form may advantageously be packaged in a pot, a tube of cream, or in a container which has flexible or deformable walls and is equipped with an orifice that can be closed with a removable cap, the composition being expelled through the orifice by pressure on the walls, or a bottle equipped with a pushbutton and a pump as indicated before.

According to one particular embodiment, a packaging article suitable for accommodating a composition according to the invention may be made of glass, metal, alloy, coated papers such as wax-coated papers, as for example papers coated with beeswax, which in particular have properties as a natural preservative.

Alternatively, a composition according to the invention may be stored under vacuum, in a hermetically closed, airtight compartment, like a vacuum-packed brick, for example, which is commonly used in the food sector.

The packaging article may be made at least partly of plastics or other suitable polymeric materials.

According to one particular embodiment, the packaging article may also be made using materials that isolate the composition from any sources of light.

The packaging article may also be made at least partly of heat insulation materials. Examples of this type of materials include fabrics, fabrics made of glass fibres coated with silicone, textiles based on ceramic fibres, cellulose fibres, polystyrene, Styrofoam, and packaging films. A cold liquid or gel may also be used as a heat insulation material.

According to one particular embodiment, the packaging article is for single use and is opened immediately prior to its use by the consumer.

According to one embodiment, a composition of the invention formulated in solid form may be packaged, for example, in a pot or in a tube for a stick, for example a lipstick tube.

Cosmetic Treatment Method

As indicated above, the invention relates to a cosmetic method intended for persons who exhibit, or are likely to exhibit, an aesthetic defect or disorder of the skin and/or its appendages that is linked to an imbalance in the differentiation and/or proliferation of the cells of an epidermis, more particularly as defined above.

A method according to the invention may further comprise a step of observing a reduction or even disappearance in the aesthetic disorder in question.

A method according to the invention may preferably be employed topically, orally, intradermally, intraepidermally or subcutaneously.

More preferably still, a method according to the invention is employed topically or orally.

A method of the invention may be employed topically, in particular by application to the skin, or its appendages, of at least one coat of a cosmetic or dermatological composition comprising as an active at least one compound of the invention, and more particularly of a cosmetic composition as defined above. Application may be carried out in particular to the skin of the face or neck and shoulders, to the scalp, to the lips, to the hair, the eyelashes or the nails, for example in the form of a mask.

A cosmetic method of the invention may be employed orally, in particular, by administration of at least one food composition for cosmetic use, comprising as an active at least one compound of the invention, and more particularly a food composition for cosmetic use as defined above.

A cosmetic method of the invention may be employed on a daily basis, for example, in the form of a single administration per day or administration twice a day, such as once in the morning and once in the evening, for example.

A cosmetic method of the invention may be employed over a period of time varying from one week to several weeks, or even several months, and this period, furthermore, may be repeated after periods of non-treatment, for a number of months or even a number of years.

As an example, a compound of the invention may be administered, for example, two to three times a day, or more, and generally over a prolonged period of at least 4 weeks, or even 4 to 15 weeks, with one or more periods of interruption where appropriate.

A method of the invention may advantageously include the administration of a composition of the invention in combination, simultaneously, successively or separately in time, with the administration of an additional cosmetic or dermatological composition, separate from the composition of the invention, and intended for the care of the scalp.

Any additional cosmetic or dermatological composition may be suitable for the invention, with the obvious proviso that its combination with a composition of the invention is not detrimental to the properties desired in the latter composition. The skilled person knows how to assess those additional cosmetic or dermatological compositions likely to be suitable, on the basis of his or her knowledge.

In the description and in the examples that follow, unless indicated otherwise, the percentages are percentages by weight and the ranges of values worded in the form "between . . . and . . . " include the lower and upper end points specified.

Before being shaped, the ingredients are mixed in the order and under conditions that are readily determined by the skilled person.

The amount and the nature of the ingredients employed in the compositions of the invention are adjusted by the skilled person so as not substantially to impair the properties required for the compositions of the invention.

The examples below are given as illustrations and do not limit the scope of the invention.

FIGURE LEGENDS

FIG. 1: illustrates HES observation of an Episkin™ model at d13 after systemic treatment over 5 days with a compound of the invention.

Figure 2:
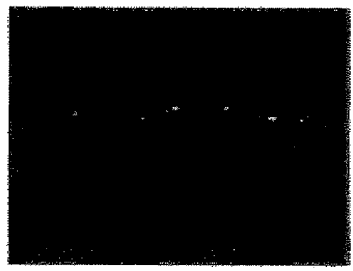
Figure 2:

FIG. 2: illustrates Ki67 immunolabelling carried out on the basis of Episkin™ samples treated in the absence and in the presence of a compound of the invention.

Figure 3:
Figure 3:
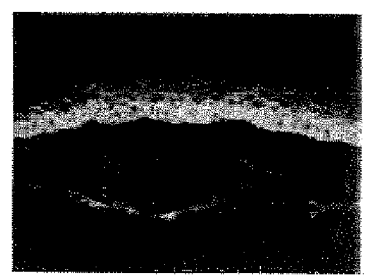

FIG. 3: illustrates CD44 immunolabelling carried out on the basis of Episkin™ samples treated in the absence and in the presence of a compound of the invention.

EXAMPLES

Example 1

Synthesis of Compounds (1) to (4) and (7)

The compounds of the invention (1) to (4) may be obtained by using a Radley system, under an inert atmosphere, with cooling equipment and a hotplate fitted with magnetic stirring. Two methods of treatment and purification may be applied.

Procedure—Compound (1)

Equipment: Radley tube equipped with magnetic stirring, placed under a nitrogen atmosphere. Ethyl benzoylacetate, 3-phenoxybenzaldehyde and 6-amino-1,3-dimethyluracil are suspended in acetic acid. The suspension is brought to reflux. Complete dissolution of the reaction medium is then observed, followed by gradual formation of the compound. The progress of the reaction is monitored by thin-layer chromatography (DCM/MeOH 90/10).

Treatment and Purification:

Method A:

The heterogeneous reaction mixture is filtered on a frit, rinsed copiously with an ethanol/water mixture (1/1) and then with ethanol. The compound is subsequently dried under reduced pressure in the presence of $P_2O_5$.

The solid is triturated with acetone (30V) for twenty minutes, filtered on a frit and then dried under reduced pressure.

Method B:

For certain reaction mixtures, the desired product does not precipitate, even in the cold. In that case the mixture is concentrated to dryness by co-evaporation with toluene, and the residue is then purified by chromatography on silica gel (dichloromethane/methanol gradient), before being triturated in isopropyl ether. Final trituration in boiling water produces the desired compounds after filtration on a frit and drying over $P_2O_5$ under reduced pressure.

Analytical Description of the Products:

Compound (1)

Reactants used: ethyl benzoylacetate, 3-phenoxybenzaldehyde, 6-amino-1,3-dimethyluracil. Purification by method B (several chromatography operations required).

Average yield: 7.8%; yellow solid.

$^1$H NMR (300 MHz, DMSO-d6): consistent

LC/MS: column: x-terra MS C18 4.6*150 mm, 5 µm, HCOOH/MeCN, tr=12.56 min, >98% at 210.0 nm; mass ESI+: $[M+Na]^+$=510.0; ESI−: $[M-H]^-$=508.0

Compound (2)

Reactants used: ethyl acetoacetate, 3-phenoxybenzaldehyde, 6-amino-1,3-dimethyluracil. Purification by method B.

Average yield: 36%; white solid.

$^1$H NMR (300 MHz, DMSO-d6): consistent

LC/MS: column: x-terra MS C18 4.6*150 mm, 5 µm, HCOOH/MeCN, tr=12.16 min, >99% at 210.0 nm; mass ESI+: $[M+N]^+$=448.2, $[M+Na]^+$=471.3; ESI−: $[M-H]^-$=446.2

Compound (3)

Reactants used: ethyl acetoacetate, benzaldehyde, 6-amino-1,3-dimethyluracil.

Purification by method B.

Average yield: 58%; white solid.

$^1$H NMR (300 MHz, DMSO-d6): consistent

LC/MS: column: x-terra MS C18 4.6*150 mm, 5 µm, HCOOH/MeCN, tr=10.57 min, >99% at 253.9 nm; mass ESI+: $[M+N]^+$=356.3, $[M+Na]^+$=378.2; ESI−: $[M-H]^-$=354.2

Compound (4)

Reactants used: ethyl acetoacetate, 3-methylbutyraldehyde, 6-amino-1,3-dimethyluracil. Purification by method B.

Average yield: 44%; white solid.

$^1$H NMR (300 MHz, DMSO-d6): consistent

LC/MS: column: x-terra MS C18 4.6*150 mm, 5 µm, HCOOH/MeCN, tr=11.29 min, >99% at 251.6 nm; mass ESI+: $[M+N]$=336.3, $[M+Na]^+$=358.3; ESI−: $[M-H]^-$=334.3.

Compound (7)

Reactants used: ethyl acetoacetate, propanaldehyde, 6-amino-1,3-dimethyluracil. Purification by method A.

Average yield: 18%; beige solid.

$^1$H NMR (300 MHz, DMSO-d6): consistent

Mass ESI+: $[M+H]^+$=308, $[M+Na]^+$=330; ESI−: $[M-H]^-$=306.

Example 2

Characterization of the Compounds of the Invention in an In Vitro Skin Model

The study took place in 3 stages:
The molecules first modelled and synthesized were used for treating kits of Episkin™ reconstructed epidermis.
Then a protein study on histological sections and on cell extracts was carried out.
In a second phase, a selection of molecules was evaluated on a RealSkin™ model.

Material & Methods

Episkin™ Reconstructed Epidermis

The reconstructed epidermises, received from the Episkin company at six days of reconstruction, were placed back into culture, when received, in 3.5 ml of differentiation medium (Episkin™ medium) under insert (in emersion) in an incubator for 48 hours (37° C., 5% $CO_2$).

The epidermises were subsequently contacted with the test compounds systemically. The Episkin™ differentiation culture medium is replaced by a differentiation medium containing the test compounds with 0.1% of final DMSO vehicle. The epidermises were placed back into culture in the incubator for 48 hours. A new systemic treatment is carried out for a further 72 hours in culture in the incubator.

For the treatment on Episkin™, each test compound was prepared at the time of use by being weighed out and dissolved at 10 mM in DMSO, then used to treat 3 samples of reconstructed epidermis. Furthermore, each compound under test was employed at a final 1 and 10 M in the culture medium (0.1% final DMSO). The positive controls used were vitamin D3, retinol and calcipotriol (a vitamin D3 analogue).

The epidermises were withdrawn (3 epidermises per treatment) for histological analysis and protein extracts (a single reconstructed epidermis is used for the histological study and the protein extract).

Histological Preparations

Morphological control of the reconstructed epidermises treated was carried out using HES (Hematoxylin—Eosin—Saffron) staining in accordance with a standard protocol on the histological sections of the samples enclosed in paraffin (toluene bath: thrice 15 minutes; 100° alcohol baths; twice one minute; 95° alcohol baths: one minute; rinsing in water baths; hematoxylin bath: once 2 minutes; rinsing in water baths; brief immersion in a hydrochloric acid bath; rinsing with water; eosin bath: once one minute; rinsing with water; brief immersion in a 100° alcohol bath; saffron bath (5 minutes); brief immersion in a 100° alcohol bath; toluene bath: thrice 2 minutes).

Fluorescent Labelling

The samples of epidermis were enclosed in OCT for freezing in liquid nitrogen and then stored at −80° C. The resulting blocks were cut to a thickness of 7 μm using a cryostat, and the slices were dried and stored at −20° C. while awaiting immunolabelling. For the labels selected, the antibodies used and their dilutions are listed in the table below:

| Ki67 anti-mouse antibody | Novocastra MM1 | Dilution 1/20 |
| CD44 anti-mouse antibody | R&D system BBA11 | Dilution 1/100 |
| α6 integrin mouse antibody | BD Pharmingen 555734 | Dilution 1/50 |

Results

Morphological Observations

FIG. 1 illustrates an HES observation of an Episkin model at d13 after systemic treatment over 5 days with the compound (4).

The effect observed on the general structure of the epidermis reveals that the compounds of the invention induce and stimulate the accelerated formation of a more thickened stratum corneum.

Results of the Immunolabelling

The labels selected for the immunolabelling are as follows:
- Ki67 to provide information on any change in cell proliferation in the basal layer, and
- CD44 to provide information on any change in the metabolism of the living layers and in the proliferation/differentiation balance.

a. Ki67

The results, illustrated by FIG. 2 with compound (4) of the invention, show that the compounds of the invention induce a strong increase in Ki67 labelling, and are therefore endowed with strong pro-proliferative properties.

b. CD44

The results, illustrated by FIG. 3 with compound (4) of the invention, show that the compounds of the invention induce an increase in CD44, corresponding to a retinoid-like effect.

Summary Table of Results

The results detailed above are summarized in the table below. For each of the parameters monitored, the rating for the most active compounds among those tested (effect greater than or less than that of the reference) is indicated by an asterisk.

The effect is generally rated for the highest concentration used (10 μM). Some compounds showed effects at lower test concentrations (1 μM). The relative classification in this table takes account of this.

| Compound | HES | Ki67 | CD44 |
|---|---|---|---|
| Vitamin D3 | 0 | 0/− | 0/+ |
| Retinol (100 μM) | 0 | 0 | + |
| Calcipotriol | ++ | — | — |
| (2) | 0 | + | 0 |
| (4) | 0 | + | ++ (*) |

Abbreviations in the Table:

HES=Hematoxylin—Eosin—Saffron (H.E.S.)

The results above reveal that the compounds of the invention are endowed with retinoid-type properties, which are particularly advantageous, for preventing and/or treating defects or disorders of the skin and/or its appendages that are linked to an imbalance in the differentiation and/or proliferation of the cells of the epidermis, and more particularly an aged skin, and/or cutaneous signs of ageing, a disorder of the barrier function of the epidermis, or a dry skin and/or signs of skin dryness.

Example 4

Beauty Cream

In accordance with a standard protocol, a face care cream of oil-in-water emulsion type is prepared, comprising:

|  | (% by weight of active substance): |
|---|---|
| Compound 7 or 4 from Example 2 | 0.5% |
| Glycerol stearate | 2% |
| Polysorbate 60 (Tween 60 from ICI) | 1% |
| Stearic acid | 1.4% |
| Triethanolamine | 0.7% |
| Carbomer | 0.4% |
| Liquid fraction of shea butter | 12% |
| Perhydrosqualene | 12% |
| Antioxidant | qs |
| Fragrance, preservative | qs |
| Water qsp | 100% |

Example 5

Anti-Ageing Gel

In accordance with a standard protocol, an anti-ageing gel for the skin is prepared, comprising:

|  | (% by weight of active substance) |
|---|---|
| Compound 7 or 4 from Example 2 | 4% |
| Hydroxypropylcellulose (Klucel H from Herculès) | 1% |
| Antioxidant | qs |
| Fragrance, preservative | qs |
| Isopropanol | 40% |
| Water | qsp 100% |

The invention claimed is:

1. A compound represented by formula IIa

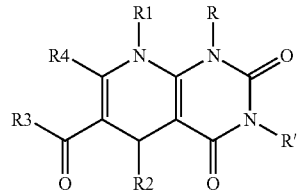

IIa in which:

$R^1$ represents H;

$R^2$ represents $C_1$-$C_4$ alkyl; or

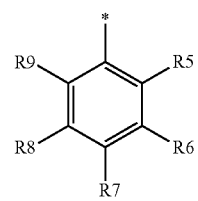

wherein $R^5$, $R^6$, $R^7$, $R^8$ and $R^9$ independently represent H or OH; or $OR^{10}$, wherein $R^{10}$ represents $C_1$-$C_4$ alkyl, $C_2$-$C_4$ alkenyl, $C_2$-$C_4$ alkynyl or phenyl;

$R^3$ represents $OR^{11}$, wherein $R^{11}$ represents H, $C_1$-$C_2$ alkyl, $C_2$ alkenyl, or $C_2$ alkynyl;

$R^4$ represents $C_2$-$C_4$ alkyl; and

R and R' independently represent H or $CH_3$;

or a physiologically acceptable salt thereof.

2. A cosmetic or dermatological composition comprising, in a physiologically acceptable medium, an effective amount of at least one compound as defined in claim 1.

3. A compound selected from the group consisting of:

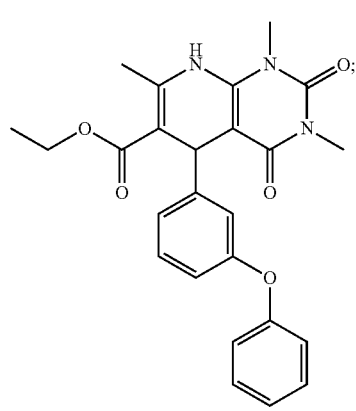

(2)

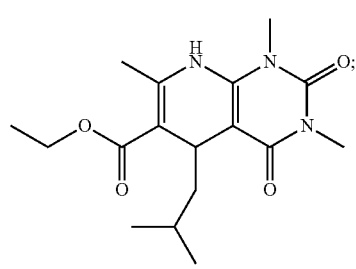

(4)

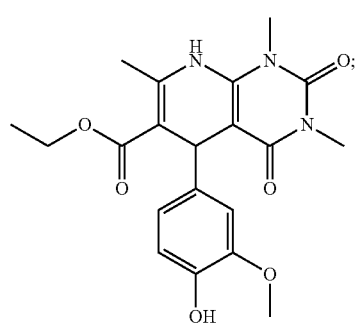

(5)

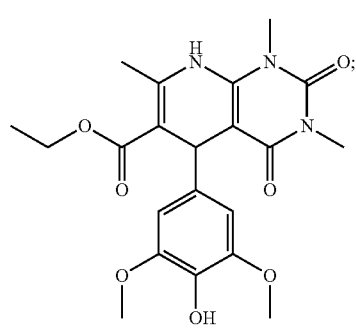

(6)

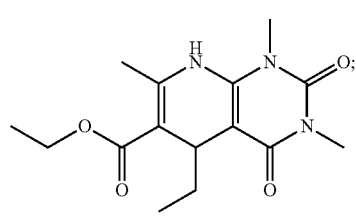

(7)

-continued

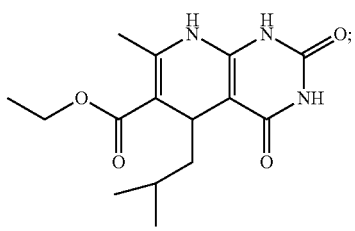
(8)

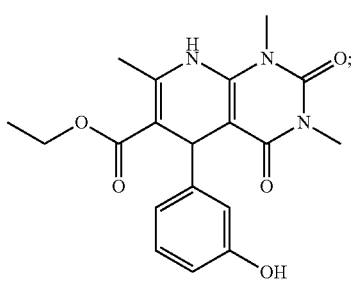
(9)

or a physiologically acceptable salt thereof.

4. A cosmetic or dermatological composition comprising, in a physiologically acceptable medium, an effective amount of at least one compound as defined in claim 3.

5. A cosmetic method, as agent for preventing and/or treating a defect in the skin and/or its appendages that is associated with an imbalance in the differentiation and/or proliferation of the cells of an epidermis in an individual in need thereof, comprising at least one step of administering to said individual at least an effective amount of at least one compound represented by formula Ia or formula Ib:

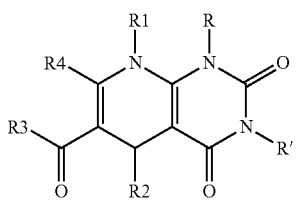
Ia

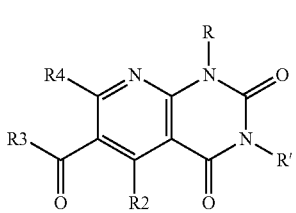
Ib in which:

$R^1$ represents H or —C(O)$R^{10}$, wherein $R^{10}$ represents $C_1$-$C_4$ alkyl, $C_2$-$C_4$ alkenyl, $C_2$-$C_4$ alkynyl, or phenyl;

$R^2$ represents H, $C_1$-$C_{12}$ alkyl, $C_2$-$C_{12}$ alkenyl, $C_2$-$C_{12}$ alkynyl, or a group selected from:

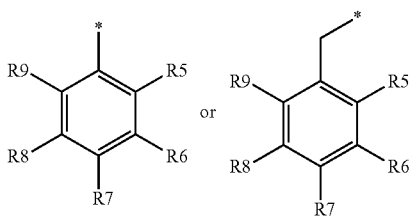

wherein $R^5$, $R^6$, $R^7$, $R^8$ and $R^9$ independently represent H, $NO_2$, OH, CN, F, Cl, Br, I, $CF_3$, $C_1$-$C_4$ alkyl, $C_2$-$C_4$ alkenyl, $C_2$-$C_4$ alkynyl or phenyl; —O-Ph-X, wherein X represents H, OH, $NO_2$, F, $C_1$-$C_4$ alkyl, $C_1$-$C_4$ alkoxy, $C_2$-$C_4$ alkenyl, $C_2$-$C_4$ alkenoxy, $C_2$-$C_4$ alkynyl or $C_2$-$C_4$ alkynoxy; or $OR^{10}$ or $OC(O)R^{10}$, wherein $R^{10}$ represents $C_1$-$C_4$ alkyl, $C_2$-$C_4$ alkenyl, $C_2$-$C_4$ alkynyl or phenyl;

$R^3$ represents $OR^{11}$, wherein $R^{11}$ represents H, $C_1$-$C_4$ alkyl, $C_2$-$C_4$ alkenyl, $C_2$-$C_4$ alkynyl, or phenyl;

$R^4$ represents $C_1$-$C_4$ alkyl, $C_2$-$C_4$ alkenyl, $C_2$-$C_4$ alkynyl, or phenyl; and R and R' independently represent H or $C_1$-$C_4$ alkyl;

or a physiologically acceptable salt thereof.

6. The method according to claim 5, where said compound is of formula Ia wherein:

$R^1$ represents H;

$R^2$ represents H, $C_1$-$C_{12}$ alkyl, $C_2$-$C_{12}$ alkenyl, $C_2$-$C_{12}$ alkynyl, or a group selected from:

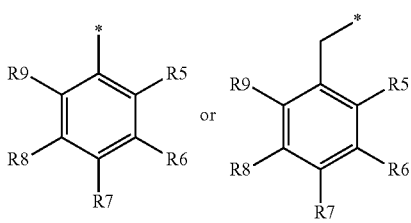

wherein $R^5$, $R^6$, $R^7$, $R^8$ and $R^9$ independently represent H, $NO_2$, OH, CN, F, Cl, Br, I, $CF_3$, $C_1$-$C_4$ alkyl, $C_2$-$C_4$ alkenyl, $C_2$-$C_4$ alkynyl or phenyl; —O-Ph-X, wherein X represents H, OH, $NO_2$, F, $C_1$-$C_4$ alkyl, $C_1$-$C_4$ alkoxy, $C_2$-$C_4$ alkenyl, $C_2$-$C_4$ alkenoxy, $C_2$-$C_4$ alkynyl or $C_2$-$C_4$ alkynoxy; or $OR^{10}$ or $OC(O)R^{10}$, wherein $R^{10}$ represents $C_1$-$C_4$ alkyl, $C_2$-$C_4$ alkenyl, $C_2$-$C_4$ alkynyl or phenyl;

$R^3$ represents $OR^{11}$, wherein $R^{11}$ represents H, $C_1$-$C_4$ alkyl, $C_2$-$C_4$ alkenyl, $C_2$-$C_4$ alkynyl, or phenyl;

$R^4$ represents $C_1$-$C_4$ alkyl, $C_2$-$C_4$ alkenyl, $C_2$-$C_4$ alkynyl, or phenyl; and R and R' independently represent H or $CH_3$;

or a physiologically acceptable salt thereof.

7. The method according to claim 5, where said compound is of formula Ia, wherein:

$R^1$ represents H;

$R^2$ represents H, $C_1$-$C_{12}$ alkyl, $C_2$-$C_{12}$ alkenyl, $C_2$-$C_{12}$ alkynyl, or a group selected from:

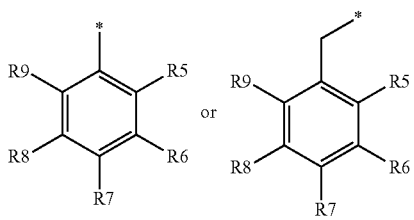

wherein $R^5$, $R^6$, $R'$, $R^8$ and $R^9$ independently represent H, OH, CN, $C_1$-$C_4$ alkyl, $C_2$-$C_4$ alkenyl, $C_2$-$C_4$ alkynyl or phenyl; or $OR^{10}$, wherein $R^{10}$ represents $C_1$-$C_4$ alkyl, $C_2$-$C_4$ alkenyl, $C_2$-$C_4$ alkynyl or phenyl;

$R^3$ represents $OR^{11}$, wherein $R^{11}$ represents H, $C_1$-$C_4$ alkyl, $C_2$-$C_4$ alkenyl, $C_2$-$C_4$ alkynyl, or phenyl;

$R^4$ represents $C_1$-$C_4$ alkyl; and

R and R' independently represent H or $CH_3$;

or a physiologically acceptable salt thereof.

8. The method according to claim 5, where said compound is of formula Ia wherein:

$R^1$ represents H;

$R^2$ represents H, $C_1$-$C_6$ alkyl, $C_2$-$C_6$ alkenyl, or $C_2$-$C_6$ alkynyl;

$R^3$ represents $OR^{11}$, wherein $R^{11}$ represents H or $C_1$-$C_4$ alkyl;

$R^4$ represents $CH_3$; and

R and R' independently represent $CH_3$;

or a physiologically acceptable salt thereof.

9. The method according to claim 5, where said compound is administered at from 0.01 to 10% by weight, relative to the total weight of a composition comprising the compound.

10. The method according to claim 5, wherein said defect in the skin is selected from the group consisting of a wrinkle, a fine line, and a deterioration in the microrelief.

11. The method according to claim 5, wherein said defect in the skin is selected from the group consisting of withered skin, flabby skin, slackened skin, sunken skin, emaciated skin, a lack of elasticity of the skin, and a lack of firmness of the skin.

12. The method according to claim 5, wherein said defect in the skin is selected from the group consisting of senile dry skin, fragile dry skin, and xerosis.

13. The method according to claim 5, wherein said defect in the skin is selected from the group consisting of dry and itchy skin, and tautness of the skin.

14. The method according to claim 5, wherein said defect in the skin is selected from the group consisting of dermatitis and ichthyosis.

15. The method according to claim 5, wherein said defect in the skin is selected from the group consisting of aged skin, dry skin, a sign of skin dryness, a cutaneous sign of ageing, and a disorder of the barrier function of the epidermis.

16. The method according to claim 15, wherein the cutaneous sign of ageing is selected from the group consisting of emaciation of the skin, a loss of firmness of the skin, a loss of elasticity of the skin, a loss of density of the skin, a loss of tonicity in the skin, a marked microrelief of the skin, a fine line, a wrinkle, a deterioration in the complexion of the skin, a wizened appearance of the skin, a deterioration in the odour of the skin, a sinking of the skin, and a withering of the skin.

17. The method according to claim 15, wherein the sign of skin dryness is selected from the group consisting of a withering of the skin, a lack of elasticity of the skin, a lack of suppleness of the skin, a lack of tonicity in the skin, coarse feeling skin, a cracking of the skin, a desquamation, a scaling of the skin, a wrinkle, and a fine line.

18. The method according to claim 5, where said compound of formula Ia is selected from:

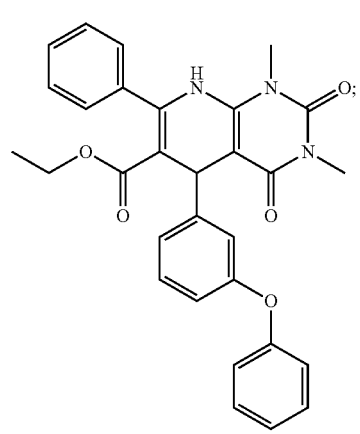

(1)

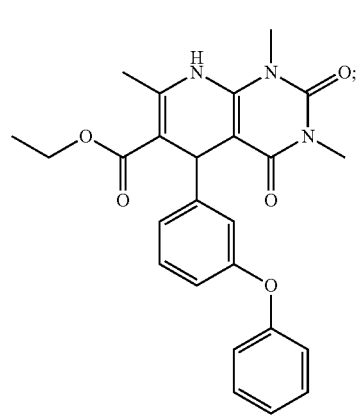

(2)

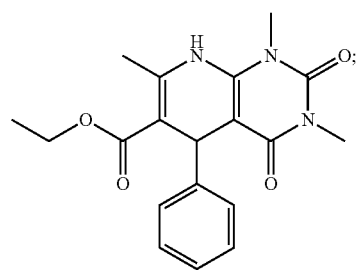

(3)

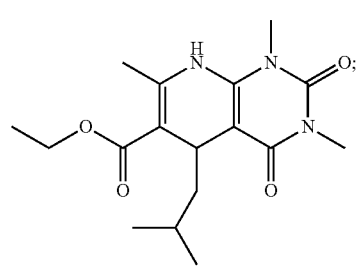

(4)

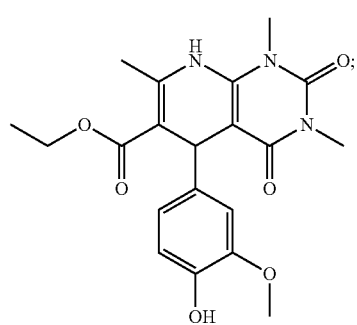
(5)
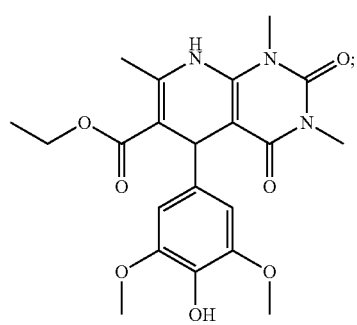
(6)
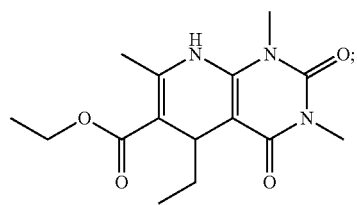
(7)
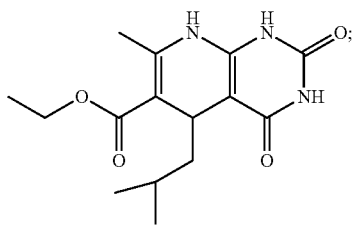
(8)
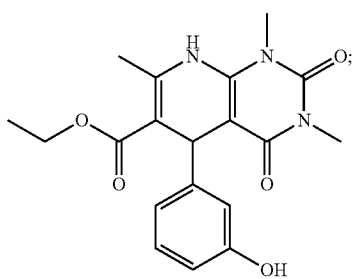
(9)
or a physiologically acceptable salt thereof.
* * * * *